(12) United States Patent
Mannheimer et al.

(10) Patent No.: US 8,452,367 B2
(45) Date of Patent: *May 28, 2013

(54) FOREHEAD SENSOR PLACEMENT

(75) Inventors: Paul D. Mannheimer, Danville, CA (US); Don L. Hannula, San Luis Obispo, CA (US); Donald E. Bebout, Lake Oswego, OR (US); Michael Patrick O'Neil, Danville, CA (US)

(73) Assignee: Covidien LP, Mansfield, MA (US)

( * ) Notice: Subject to any disclaimer, the term of this patent is extended or adjusted under 35 U.S.C. 154(b) by 212 days.

This patent is subject to a terminal disclaimer.

(21) Appl. No.: 12/843,651

(22) Filed: Jul. 26, 2010

(65) Prior Publication Data

US 2011/0009723 A1 Jan. 13, 2011

Related U.S. Application Data

(60) Continuation of application No. 11/495,195, filed on Jul. 28, 2006, now Pat. No. 7,822,453, which is a division of application No. 10/678,040, filed on Oct. 1, 2003, now Pat. No. 7,289,837.

(60) Provisional application No. 60/415,468, filed on Oct. 1, 2002.

(51) Int. Cl.
*A61B 5/1455* (2006.01)

(52) U.S. Cl.
USPC .......................................... 600/344; 600/340

(58) Field of Classification Search
USPC ........................... 600/310, 322, 323, 340, 344
See application file for complete search history.

(56) References Cited

U.S. PATENT DOCUMENTS

| 1,304,215 | A | * | 5/1919 | Snyder | 2/181 |
|---|---|---|---|---|---|
| 1,899,020 | A | * | 2/1933 | Drueding | 2/181 |
| 4,025,733 | A | | 5/1977 | Klar et al. | |
| 4,047,400 | A | | 9/1977 | Thorneburg | |
| 4,321,930 | A | | 3/1982 | Jobsis et al. | |
| 4,462,116 | A | | 7/1984 | Sanzone et al. | |

(Continued)

FOREIGN PATENT DOCUMENTS

| CN | 1306260 | 8/2001 |
|---|---|---|
| CN | 1657007 | 8/2005 |

(Continued)

*Primary Examiner* — Eric Winakur
(74) *Attorney, Agent, or Firm* — Fletcher Yoder

(57) ABSTRACT

Forehead oximetry sensor devices and methods for determining physiological parameters using forehead oximetry sensors. One method includes placing an oximetry sensor on the forehead of a patient, such that the sensor is placed on the lower forehead region, above the eyebrow with the sensor optics placed lateral of the iris and proximal the temple; and operating the pulse oximeter to obtain the physiological parameter. In one aspect, the method also includes providing and placing a headband over the oximetry sensor, or alternately, the sensor is a headband-integrated sensor. The headband has an elastic segment sized to fit around the patient's head. The headband also includes a non-elastic segment that is smaller than and attached with the elastic segment. The non-elastic segment is sized to span a portion of the elastic segment when the elastic segment is stretched. In addition, the non-elastic segment is larger than the portion of the elastic segment it spans when the elastic segment is not stretched. When the headband or the headband-integrated sensor is sufficiently tight, it delivers a pressure in the range higher than the venous pressure and lower than the capillary pressure to the forehead of the patient.

18 Claims, 8 Drawing Sheets

U.S. PATENT DOCUMENTS

| | | |
|---|---|---|
| 4,499,741 A | 2/1985 | Harris |
| 4,510,938 A | 4/1985 | Jobsis et al. |
| 4,570,638 A | 2/1986 | Stoddart et al. |
| 4,675,919 A | 6/1987 | Heine et al. |
| 4,739,757 A | 4/1988 | Edwards |
| 4,775,116 A | 10/1988 | Klein |
| 4,784,162 A | 11/1988 | Ricks et al. |
| 4,802,486 A | 2/1989 | Bowers et al. |
| 4,825,872 A | 5/1989 | Tan et al. |
| 4,825,879 A | 5/1989 | Tan et al. |
| 4,833,734 A | 5/1989 | Der Estephanian |
| 4,838,279 A | 6/1989 | Fore |
| 4,856,116 A | 8/1989 | Sullivan |
| 4,890,619 A | 1/1990 | Hatschek |
| 4,910,804 A | 3/1990 | Lidgren |
| 4,911,167 A | 3/1990 | Corenman et al. |
| 4,918,758 A | 4/1990 | Rendina |
| 4,930,888 A | 6/1990 | Feisleben et al. |
| 4,942,877 A | 7/1990 | Sakai et al. |
| 4,972,331 A | 11/1990 | Chance |
| 4,977,011 A | 12/1990 | Smith |
| 4,991,234 A | 2/1991 | Greenberg |
| 4,996,975 A | 3/1991 | Nakamura |
| 5,005,374 A | 4/1991 | Spitler et al. |
| 5,054,488 A | 10/1991 | Muz |
| 5,080,096 A | 1/1992 | Hooper et al. |
| 5,080,098 A | 1/1992 | Willett et al. |
| H1039 H | 4/1992 | Tripp, Jr. et al. |
| 5,111,817 A | 5/1992 | Clark et al. |
| 5,119,815 A | 6/1992 | Chance |
| 5,122,974 A | 6/1992 | Chance |
| 5,125,403 A | 6/1992 | Culp |
| 5,167,230 A | 12/1992 | Chance |
| 5,188,108 A | 2/1993 | Secker |
| 5,191,891 A | 3/1993 | Righter |
| 5,209,230 A | 5/1993 | Swedlow et al. |
| 5,214,409 A | 5/1993 | Beigel |
| 5,217,012 A | 6/1993 | Young et al. |
| 5,217,013 A | 6/1993 | Lewis et al. |
| 5,241,300 A | 8/1993 | Buschmann |
| 5,246,003 A | 9/1993 | DeLonzor |
| 5,253,645 A | 10/1993 | Friedman et al. |
| 5,267,563 A | 12/1993 | Swedlow et al. |
| 5,267,567 A | 12/1993 | Aung et al. |
| 5,295,490 A | 3/1994 | Dodakian |
| 5,313,940 A | 5/1994 | Fuse et al. |
| 5,337,744 A | 8/1994 | Branigan |
| 5,348,008 A | 9/1994 | Bornn et al. |
| 5,353,798 A | 10/1994 | Sieben |
| 5,354,979 A | 10/1994 | Adelson et al. |
| 5,357,953 A | 10/1994 | Merrick et al. |
| 5,368,025 A | 11/1994 | Young et al. |
| 5,368,562 A | 11/1994 | Blomquist et al. |
| 5,369,808 A * | 12/1994 | Brewer et al. ............... 2/181.4 |
| 5,383,874 A | 1/1995 | Jackson et al. |
| 5,392,777 A | 2/1995 | Swedlow et al. |
| 5,398,689 A | 3/1995 | Conner et al. |
| 5,400,267 A | 3/1995 | Denen et al. |
| 5,405,269 A | 4/1995 | Stupecky |
| 5,405,614 A | 4/1995 | D'Angelo et al. |
| 5,413,099 A | 5/1995 | Schmidt et al. |
| 5,413,101 A | 5/1995 | Sugiura |
| 5,413,102 A | 5/1995 | Schmidt et al. |
| 5,415,166 A | 5/1995 | Imran |
| 5,425,360 A | 6/1995 | Nelson |
| 5,431,170 A | 7/1995 | Mathews |
| 5,437,275 A | 8/1995 | Amundsen et al. |
| 5,437,634 A | 8/1995 | Amano |
| 5,444,254 A | 8/1995 | Thomson |
| 5,451,763 A | 9/1995 | Pickett et al. |
| 5,452,717 A | 9/1995 | Branigan et al. |
| 5,465,714 A | 11/1995 | Scheuing |
| 5,469,845 A | 11/1995 | DeLonzor et al. |
| 5,482,034 A | 1/1996 | Lewis et al. |
| 5,490,523 A | 2/1996 | Isaacson et al. |
| 5,507,752 A | 4/1996 | Elliott |
| 5,528,519 A | 6/1996 | Ohkura et al. |
| 5,546,955 A | 8/1996 | Wilk |
| 5,551,423 A | 9/1996 | Sugiura |
| 5,562,718 A | 10/1996 | Palermo |
| 5,564,108 A | 10/1996 | Hunsaker et al. |
| 5,564,417 A | 10/1996 | Chance |
| 5,584,296 A | 12/1996 | Cui et al. |
| 5,592,408 A | 1/1997 | Keskin et al. |
| 5,596,987 A | 1/1997 | Chance |
| 5,617,865 A | 4/1997 | Palczewska et al. |
| 5,617,866 A | 4/1997 | Marian, Jr. |
| 5,627,323 A | 5/1997 | Stern |
| 5,634,466 A | 6/1997 | Gruner |
| 5,638,593 A | 6/1997 | Gerhardt et al. |
| 5,638,818 A | 6/1997 | Diab et al. |
| 5,640,953 A | 6/1997 | Bishop et al. |
| 5,645,059 A | 7/1997 | Fine et al. |
| 5,645,440 A | 7/1997 | Tobler et al. |
| 5,645,586 A | 7/1997 | Meltzer |
| 5,646,416 A | 7/1997 | Van De Velde |
| 5,671,750 A | 9/1997 | Shinoda |
| 5,673,708 A | 10/1997 | Athanasiou et al. |
| 5,678,544 A | 10/1997 | DeLonzor et al. |
| 5,681,285 A | 10/1997 | Ford et al. |
| 5,683,434 A | 11/1997 | Archer |
| 5,697,363 A | 12/1997 | Hart |
| 5,697,367 A | 12/1997 | Lewis et al. |
| 5,701,894 A | 12/1997 | Cherry et al. |
| 5,706,820 A | 1/1998 | Hossack et al. |
| 5,732,475 A | 3/1998 | Sacks et al. |
| 5,738,612 A | 4/1998 | Tsuda |
| 5,743,856 A | 4/1998 | Oka et al. |
| 5,743,857 A | 4/1998 | Shinoda et al. |
| 5,752,913 A | 5/1998 | Oka |
| 5,752,920 A | 5/1998 | Ogura et al. |
| 5,758,644 A | 6/1998 | Diab et al. |
| 5,772,601 A | 6/1998 | Oka et al. |
| 5,776,058 A | 7/1998 | Levinson et al. |
| 5,776,071 A | 7/1998 | Inukai et al. |
| 5,779,631 A | 7/1998 | Chance |
| 5,779,639 A | 7/1998 | Yeung |
| 5,782,757 A | 7/1998 | Diab et al. |
| 5,786,592 A | 7/1998 | Hök |
| 5,791,347 A | 8/1998 | Flaherty et al. |
| 5,791,348 A | 8/1998 | Aung et al. |
| 5,792,052 A | 8/1998 | Isaacson et al. |
| 5,792,058 A | 8/1998 | Lee et al. |
| 5,797,841 A | 8/1998 | Delonzor et al. |
| 5,810,724 A | 9/1998 | Gronvall |
| 5,813,980 A | 9/1998 | Levinson et al. |
| 5,817,008 A | 10/1998 | Rafert et al. |
| 5,823,012 A | 10/1998 | Hacskaylo |
| 5,823,952 A | 10/1998 | Levinson et al. |
| 5,826,277 A | 10/1998 | McConville |
| 5,830,136 A | 11/1998 | Delonzor et al. |
| 5,830,137 A | 11/1998 | Scharf |
| 5,830,148 A | 11/1998 | Inukai et al. |
| 5,830,149 A | 11/1998 | Oka et al. |
| 5,833,602 A | 11/1998 | Osemwota |
| 5,836,887 A | 11/1998 | Oka et al. |
| 5,839,439 A | 11/1998 | Nierlich et al. |
| RE36,000 E | 12/1998 | Swedlow et al. |
| 5,842,981 A | 12/1998 | Larsen et al. |
| 5,842,982 A | 12/1998 | Mannheimer |
| 5,851,179 A | 12/1998 | Ritson et al. |
| 5,853,364 A | 12/1998 | Baker, Jr. et al. |
| 5,857,974 A | 1/1999 | Eberle et al. |
| 5,860,932 A | 1/1999 | Goto et al. |
| 5,860,957 A | 1/1999 | Jacobsen et al. |
| 5,868,133 A | 2/1999 | DeVries et al. |
| 5,870,626 A | 2/1999 | Lebeau |
| 5,872,713 A | 2/1999 | Douglas et al. |
| 5,873,821 A | 2/1999 | Chance et al. |
| 5,879,294 A | 3/1999 | Anderson et al. |
| 5,891,021 A | 4/1999 | Dillon et al. |
| 5,891,026 A | 4/1999 | Wang et al. |
| 5,895,359 A | 4/1999 | Peel |
| 5,902,235 A | 5/1999 | Lewis et al. |
| 5,906,581 A | 5/1999 | Tsuda |
| 5,913,819 A | 6/1999 | Taylor et al. |
| 5,916,154 A | 6/1999 | Hobbs et al. |

| Patent Number | Kind | Date | Inventor |
|---|---|---|---|
| 5,919,133 | A | 7/1999 | Taylor et al. |
| 5,931,789 | A | 8/1999 | Alfano et al. |
| 5,931,790 | A | 8/1999 | Peel |
| 5,931,791 | A | 8/1999 | Saltzstein et al. |
| 5,934,925 | A | 8/1999 | Tobler et al. |
| 5,936,539 | A | 8/1999 | Fuchs |
| 5,947,905 | A | 9/1999 | Hadjicostis et al. |
| 5,954,053 | A | 9/1999 | Chance et al. |
| 5,957,850 | A | 9/1999 | Marian, Jr. et al. |
| 5,964,701 | A | 10/1999 | Asada et al. |
| 5,980,464 | A | 11/1999 | Tsuda |
| 5,983,129 | A | 11/1999 | Cowan et al. |
| 5,987,343 | A | 11/1999 | Kinast |
| 5,987,351 | A | 11/1999 | Chance |
| 5,991,648 | A | 11/1999 | Levin |
| 5,995,077 | A | 11/1999 | Wilcox et al. |
| 5,995,855 | A | 11/1999 | Kiani et al. |
| 5,995,856 | A | 11/1999 | Mannheimer et al. |
| 5,995,857 | A | 11/1999 | Toomim et al. |
| 6,007,492 | A | 12/1999 | Goto et al. |
| 6,011,986 | A | 1/2000 | Diab et al. |
| 6,022,320 | A | 2/2000 | Ogura et al. |
| 6,027,453 | A | 2/2000 | Miwa et al. |
| 6,030,351 | A | 2/2000 | Schmidt et al. |
| 6,031,603 | A | 2/2000 | Fine et al. |
| 6,036,651 | A | 3/2000 | Inukai et al. |
| 6,041,247 | A | 3/2000 | Weckstrom et al. |
| 6,047,201 | A | 4/2000 | Jackson |
| 6,047,203 | A | 4/2000 | Sackner et al. |
| 6,049,958 | A | 4/2000 | Eberle et al. |
| 6,050,951 | A | 4/2000 | Friedman et al. |
| 6,052,619 | A | 4/2000 | John |
| 6,073,038 | A | 6/2000 | Wang et al. |
| 6,084,380 | A | 7/2000 | Burton |
| 6,085,752 | A | 7/2000 | Kehr et al. |
| 6,088,607 | A | 7/2000 | Diab et al. |
| 6,106,780 | A | 8/2000 | Douglas et al. |
| 6,112,107 | A | 8/2000 | Hannula |
| 6,115,621 | A | 9/2000 | Chin |
| 6,118,382 | A | 9/2000 | Hibbs et al. |
| 6,134,459 | A | 10/2000 | Roberts et al. |
| 6,144,868 | A | 11/2000 | Parker |
| 6,149,481 | A | 11/2000 | Wang et al. |
| 6,152,754 | A | 11/2000 | Gerhardt et al. |
| 6,154,667 | A | 11/2000 | Miura et al. |
| 6,162,188 | A | 12/2000 | Barnea |
| 6,165,173 | A | 12/2000 | Kamdar et al. |
| 6,171,258 | B1 | 1/2001 | Karakasoglu et al. |
| 6,173,196 | B1 | 1/2001 | Delonzor et al. |
| 6,179,786 | B1 | 1/2001 | Young |
| 6,181,959 | B1 | 1/2001 | Schollermann et al. |
| 6,184,521 | B1 | 2/2001 | Coffin, IV et al. |
| 6,186,953 | B1 | 2/2001 | Narimatsu |
| 6,186,954 | B1 | 2/2001 | Narimatsu |
| 6,190,325 | B1 | 2/2001 | Narimatsu |
| 6,196,974 | B1 | 3/2001 | Miwa |
| 6,198,952 | B1 | 3/2001 | Miesel |
| 6,199,550 | B1 | 3/2001 | Wiesmann et al. |
| 6,209,144 | B1 | 4/2001 | Carter |
| 6,216,021 | B1 | 4/2001 | Franceschini et al. |
| 6,223,063 | B1 | 4/2001 | Chaiken et al. |
| 6,241,680 | B1 | 6/2001 | Miwa |
| 6,248,083 | B1 | 6/2001 | Smith et al. |
| 6,251,076 | B1 | 6/2001 | Hovland et al. |
| 6,251,080 | B1 | 6/2001 | Henkin et al. |
| 6,251,081 | B1 | 6/2001 | Narimatsu |
| 6,251,113 | B1 | 6/2001 | Appelbaum et al. |
| 6,256,523 | B1 | 7/2001 | Diab et al. |
| 6,256,524 | B1 | 7/2001 | Walker et al. |
| 6,263,221 | B1 | 7/2001 | Chance et al. |
| 6,263,223 | B1 | 7/2001 | Shepherd et al. |
| 6,280,213 | B1 | 8/2001 | Tobler et al. |
| 6,282,450 | B1 | 8/2001 | Hartlaub et al. |
| 6,283,922 | B1 | 9/2001 | Goto et al. |
| 6,285,895 | B1 | 9/2001 | Ristolainen et al. |
| 6,306,076 | B1 | 10/2001 | Gill |
| 6,308,089 | B1 | 10/2001 | von der Ruhr et al. |
| 6,321,100 | B1 | 11/2001 | Parker |
| 6,322,516 | B1 | 11/2001 | Masuda et al. |
| 6,343,223 | B1 | 1/2002 | Chin et al. |
| 6,343,224 | B1 | 1/2002 | Parker |
| 6,346,886 | B1 | 2/2002 | De La Huerga |
| 6,349,228 | B1 | 2/2002 | Kiani et al. |
| 6,356,774 | B1 | 3/2002 | Bernstein et al. |
| 6,362,622 | B1 | 3/2002 | Stauber et al. |
| 6,368,282 | B1 | 4/2002 | Oka et al. |
| 6,370,411 | B1 | 4/2002 | Osadchy et al. |
| 6,377,829 | B1 | 4/2002 | Al-Ali |
| 6,381,480 | B1 | 4/2002 | Kuroyama Yukio |
| 6,381,481 | B1 | 4/2002 | Levendowski et al. |
| 6,385,486 | B1 | 5/2002 | John et al. |
| 6,385,821 | B1 | 5/2002 | Modgil et al. |
| 6,387,092 | B1 | 5/2002 | Burnside et al. |
| 6,388,240 | B2 | 5/2002 | Schulz et al. |
| 6,397,091 | B1 | 5/2002 | Diab et al. |
| 6,405,075 | B1 | 6/2002 | Levin |
| 6,416,471 | B1 | 7/2002 | Kumar et al. |
| 6,416,474 | B1 | 7/2002 | Penner et al. |
| 6,417,774 | B1 | 7/2002 | Hibbs et al. |
| 6,423,010 | B1 | 7/2002 | Friedman et al. |
| 6,430,423 | B2 | 8/2002 | DeLonzor et al. |
| 6,432,050 | B1 | 8/2002 | Porat et al. |
| 6,450,168 | B1 | 9/2002 | Nguyen |
| 6,450,957 | B1 | 9/2002 | Yoshimi et al. |
| 6,450,981 | B1 | 9/2002 | Shabty et al. |
| 6,454,708 | B1 | 9/2002 | Ferguson et al. |
| 6,456,862 | B2 | 9/2002 | Benni |
| 6,461,305 | B1 | 10/2002 | Schnall |
| 6,463,310 | B1 | 10/2002 | Swedlow et al. |
| 6,466,809 | B1 | 10/2002 | Riley |
| 6,468,241 | B1 | 10/2002 | Gelfand et al. |
| 6,470,199 | B1 | 10/2002 | Kopotic et al. |
| 6,470,279 | B1 | 10/2002 | Samsoondar |
| 6,480,762 | B1 | 11/2002 | Uchikubo et al. |
| 6,491,638 | B2 | 12/2002 | Oka |
| 6,491,639 | B1 | 12/2002 | Turcott |
| 6,503,087 | B1 | 1/2003 | Eggert et al. |
| 6,503,204 | B1 | 1/2003 | Sumanaweera et al. |
| 6,505,061 | B2 | 1/2003 | Larson |
| 6,511,478 | B1 | 1/2003 | Burnside et al. |
| 6,516,289 | B2 | 2/2003 | David |
| 6,519,487 | B1 | 2/2003 | Parker |
| 6,524,257 | B2 | 2/2003 | Ogura |
| 6,525,386 | B1 | 2/2003 | Mills et al. |
| 6,526,309 | B1 | 2/2003 | Chance |
| 6,526,970 | B2 | 3/2003 | DeVries et al. |
| 6,527,725 | B1 | 3/2003 | Inuaki et al. |
| 6,527,726 | B2 | 3/2003 | Goto et al. |
| 6,535,765 | B1 | 3/2003 | Amely-Velez et al. |
| 6,537,220 | B1 | 3/2003 | Friemel et al. |
| 6,541,756 | B2 | 4/2003 | Schulz et al. |
| 6,542,081 | B2 | 4/2003 | Torch |
| 6,547,742 | B2 | 4/2003 | Oka et al. |
| 6,547,743 | B2 | 4/2003 | Brydon |
| 6,551,252 | B2 | 4/2003 | Sackner et al. |
| 6,553,242 | B1 | 4/2003 | Sarussi |
| 6,575,902 | B1 | 6/2003 | Burton |
| 6,575,904 | B2 | 6/2003 | Nagai et al. |
| 6,577,884 | B1 | 6/2003 | Boas |
| 6,580,086 | B1 | 6/2003 | Schulz et al. |
| 6,582,371 | B2 | 6/2003 | Miller |
| 6,582,374 | B2 | 6/2003 | Yokozeki |
| 6,584,356 | B2 | 6/2003 | Wassmund et al. |
| 6,589,171 | B2 | 7/2003 | Keirsbilck |
| 6,589,183 | B2 | 7/2003 | Yokozeki |
| 6,589,189 | B2 | 7/2003 | Meyerson et al. |
| 6,594,513 | B1 | 7/2003 | Jobsis et al. |
| 6,597,933 | B2 | 7/2003 | Kiani et al. |
| 6,605,038 | B1 | 8/2003 | Teller et al. |
| 6,606,993 | B1 | 8/2003 | Wiesmann et al. |
| 6,611,793 | B1 | 8/2003 | Burnside et al. |
| 6,615,065 | B1 | 9/2003 | Barrett et al. |
| 6,622,034 | B1 | 9/2003 | Gorski et al. |
| 6,626,537 | B1 | 9/2003 | Odom et al. |
| 6,635,048 | B1 | 10/2003 | Ullestad et al. |
| 6,640,116 | B2 | 10/2003 | Diab |
| 6,645,154 | B2 | 11/2003 | Oka |
| 6,645,155 | B2 | 11/2003 | Inuaki et al. |

| | | | | | |
|---|---|---|---|---|---|
| 6,653,557 B2 | 11/2003 | Wolf et al. | 6,952,870 B2 | 10/2005 | Miller |
| 6,654,622 B1 | 11/2003 | Eberhard et al. | 6,955,650 B2 | 10/2005 | Mault et al. |
| 6,662,033 B2 | 12/2003 | Casciani et al. | 6,965,071 B2 | 11/2005 | Watchko et al. |
| 6,666,860 B1 | 12/2003 | Takahashi | 6,971,790 B2 | 12/2005 | Quinn et al. |
| 6,671,531 B2 | 12/2003 | Al-Ali et al. | 6,979,329 B2 | 12/2005 | Burnside et al. |
| 6,671,545 B2 | 12/2003 | Fincke | 6,985,763 B2 | 1/2006 | Boas et al. |
| 6,678,543 B2 | 1/2004 | Diab et al. | 6,985,764 B2 | 1/2006 | Mason et al. |
| 6,681,454 B2 | 1/2004 | Modgil et al. | 6,990,371 B2 | 1/2006 | Powers et al. |
| 6,684,091 B2 | 1/2004 | Parker | 6,993,371 B2 | 1/2006 | Kiani et al. |
| 6,694,160 B2 | 2/2004 | Chin | 6,995,665 B2 | 2/2006 | Appelt et al. |
| 6,695,806 B2 | 2/2004 | Gelfand et al. | 7,001,334 B2 | 2/2006 | Reed et al. |
| 6,700,497 B2 | 3/2004 | Hibbs et al. | 7,017,420 B2 | 3/2006 | Kalvesten et al. |
| 6,704,601 B1 | 3/2004 | Amely-Velez et al. | 7,018,338 B2 | 3/2006 | Vetter et al. |
| 6,708,048 B1 | 3/2004 | Chance | 7,019,392 B2 | 3/2006 | Iwaskai |
| 6,711,425 B1 | 3/2004 | Reuss | 7,020,508 B2 | 3/2006 | Stivoric et al. |
| 6,712,767 B2 | 3/2004 | Hossack et al. | 7,024,235 B2 | 4/2006 | Melker et al. |
| 6,721,585 B1 | 4/2004 | Parker | 7,027,850 B2 | 4/2006 | Wasserman |
| 6,721,602 B2 | 4/2004 | Engmark et al. | 7,027,871 B2 | 4/2006 | Burnes et al. |
| 6,725,075 B2 | 4/2004 | Al-Ali | 7,033,316 B2 | 4/2006 | Takahashi |
| 6,726,327 B2 | 4/2004 | Torrey et al. | 7,039,449 B2 | 5/2006 | Al-Ali |
| 6,731,963 B2 | 5/2004 | Finarov et al. | 7,041,121 B1 | 5/2006 | Williams et al. |
| 6,735,459 B2 | 5/2004 | Parker | 7,047,054 B2 | 5/2006 | Benni |
| 6,736,759 B1 | 5/2004 | Stubbs et al. | 7,047,055 B2 | 5/2006 | Boas et al. |
| 6,736,786 B1 | 5/2004 | Shabty et al. | 7,047,056 B2 | 5/2006 | Hannula et al. |
| 6,743,173 B2 | 6/2004 | Penner et al. | 7,048,687 B1 | 5/2006 | Reuss et al. |
| 6,743,202 B2 | 6/2004 | Hirschman et al. | 7,052,509 B2 | 5/2006 | Lennox |
| 6,745,061 B1 | 6/2004 | Hicks et al. | 7,054,453 B2 | 5/2006 | Causevic et al. |
| 6,748,254 B2 | 6/2004 | O'Neil et al. | 7,054,454 B2 | 5/2006 | Causevic et al. |
| 6,748,262 B2 | 6/2004 | Harada et al. | 7,063,669 B2 | 6/2006 | Brawner et al. |
| 6,749,567 B2 | 6/2004 | Davis | 7,067,893 B2 | 6/2006 | Mills et al. |
| 6,755,789 B2 | 6/2004 | Stringer et al. | 7,072,704 B2 | 7/2006 | Bucholz |
| 6,758,808 B2 | 7/2004 | Paul | 7,079,036 B2 | 7/2006 | Cooper et al. |
| 6,763,255 B2 | 7/2004 | DeLonzor et al. | 7,081,128 B2 | 7/2006 | Hart et al. |
| 6,767,330 B2 | 7/2004 | Lavery | 7,085,597 B2 | 8/2006 | Fein et al. |
| 6,771,994 B2 | 8/2004 | Kiani et al. | 7,107,706 B1 | 9/2006 | Bailey |
| 6,776,758 B2 | 8/2004 | Peszynski et al. | 7,113,815 B2 | 9/2006 | O'Neil et al. |
| 6,779,257 B2 | 8/2004 | Kiepen et al. | 7,132,641 B2 | 11/2006 | Schulz et al. |
| 6,785,568 B2 | 8/2004 | Chance | 7,171,251 B2 | 1/2007 | Sarussi et al. |
| 6,792,300 B1 | 9/2004 | Diab et al. | 7,181,264 B2 | 2/2007 | Wiesmann et al. |
| 6,796,946 B2 | 9/2004 | Ogura et al. | 7,204,250 B1 | 4/2007 | Burton |
| 6,801,799 B2 | 10/2004 | Mendelson | 7,220,220 B2 | 5/2007 | Stubbs et al. |
| 6,804,543 B2 | 10/2004 | Miller et al. | 7,245,953 B1 | 7/2007 | Parker |
| 6,804,558 B2 | 10/2004 | Haller et al. | 7,248,910 B2 | 7/2007 | Li et al. |
| 6,808,496 B2 | 10/2004 | Oka et al. | 7,289,837 B2 | 10/2007 | Mannheimer et al. |
| 6,811,538 B2 | 11/2004 | Westbrook et al. | 7,297,119 B2 | 11/2007 | Westbrook et al. |
| 6,813,511 B2 | 11/2004 | Diab et al. | 7,313,427 B2 | 12/2007 | Benni |
| 6,824,520 B2 | 11/2004 | Orr et al. | 7,349,726 B2 | 3/2008 | Casciani et al. |
| 6,827,688 B2 | 12/2004 | Goto et al. | 7,376,454 B2 | 5/2008 | Casciani et al. |
| 6,829,003 B2 | 12/2004 | Takami | 7,413,305 B2 | 8/2008 | Baumann et al. |
| 6,830,711 B2 | 12/2004 | Mills et al. | 7,415,298 B2 | 8/2008 | Casciani et al. |
| 6,832,987 B2 | 12/2004 | David et al. | 7,698,909 B2 | 4/2010 | Hannula et al. |
| 6,842,722 B2 | 1/2005 | David | 2001/0000790 A1 | 5/2001 | DeLonzor et al. |
| 6,847,294 B1 | 1/2005 | Lin et al. | 2001/0009398 A1 | 7/2001 | Sekura et al. |
| 6,849,074 B2 | 2/2005 | Chen et al. | 2002/0013538 A1 | 1/2002 | Teller |
| 6,853,304 B2 | 2/2005 | Reisman et al. | 2002/0042558 A1 | 4/2002 | Mendelson |
| 6,870,479 B2 | 3/2005 | Gabriel | 2002/0052539 A1 | 5/2002 | Haller et al. |
| 6,875,176 B2 | 4/2005 | Mourad et al. | 2002/0084904 A1 | 7/2002 | De La Huerga |
| 6,877,511 B2 | 4/2005 | DeVries et al. | 2002/0091335 A1 | 7/2002 | John et al. |
| 6,893,400 B2 | 5/2005 | Kawaguchi et al. | 2002/0095087 A1 | 7/2002 | Mourad et al. |
| 6,898,299 B1 | 5/2005 | Brooks | 2002/0095092 A1 | 7/2002 | Kondo et al. |
| 6,899,682 B2 | 5/2005 | Eberle et al. | 2002/0103445 A1 | 8/2002 | Rahdert et al. |
| 6,899,684 B2 | 5/2005 | Mault et al. | 2002/0109600 A1 | 8/2002 | Mault et al. |
| 6,904,124 B2 | 6/2005 | Staver et al. | 2002/0124295 A1 | 9/2002 | Fenwick et al. |
| 6,907,284 B2 | 6/2005 | Hamilton et al. | 2002/0135488 A1 | 9/2002 | Hibbs et al. |
| 6,909,912 B2 | 6/2005 | Melker | 2002/0139368 A1 | 10/2002 | Bachinski |
| 6,911,027 B1 | 6/2005 | Edwards et al. | 2002/0148470 A1 | 10/2002 | Blue et al. |
| 6,915,167 B2 | 7/2005 | Splett et al. | 2002/0151929 A1 | 10/2002 | Goto et al. |
| 6,920,345 B2 | 7/2005 | Al-Ali et al. | 2002/0156354 A1 | 10/2002 | Larson |
| 6,921,198 B2 | 7/2005 | Gruszecki et al. | 2002/0161290 A1 | 10/2002 | Chance |
| 6,923,771 B2 | 8/2005 | Ogura et al. | 2002/0161309 A1 | 10/2002 | Marro |
| 6,923,776 B2 | 8/2005 | Shabty et al. | 2002/0165462 A1 | 11/2002 | Westbrook et al. |
| 6,930,608 B2 | 8/2005 | Grajales et al. | 2002/0173706 A1 | 11/2002 | Takatani et al. |
| 6,934,570 B2 | 8/2005 | Kiani et al. | 2002/0173708 A1 | 11/2002 | DeLonzor et al. |
| 6,934,571 B2 | 8/2005 | Wiesmann et al. | 2003/0004547 A1 | 1/2003 | Owens et al. |
| 6,936,011 B2 | 8/2005 | Sheldon | 2003/0009119 A1 | 1/2003 | Kamm et al. |
| 6,938,488 B2 | 9/2005 | Diaz et al. | 2003/0009308 A1 | 1/2003 | Kirtley |
| 6,939,314 B2 | 9/2005 | Hall et al. | 2003/0018243 A1 | 1/2003 | Gerhardt et al. |
| 6,943,881 B2 | 9/2005 | Wang | 2003/0023140 A1 | 1/2003 | Chance |
| 6,944,498 B2 | 9/2005 | Owens et al. | 2003/0036685 A1 | 2/2003 | Goodman |

| Publication No. | Date | Inventor |
|---|---|---|
| 2003/0062046 A1 | 4/2003 | Wiesmann et al. |
| 2003/0065273 A1 | 4/2003 | Mault et al. |
| 2003/0065274 A1 | 4/2003 | Mault et al. |
| 2003/0065275 A1 | 4/2003 | Mault et al. |
| 2003/0086156 A1 | 5/2003 | McGuire |
| 2003/0109775 A1 | 6/2003 | O'Neil et al. |
| 2003/0120183 A1 | 6/2003 | Simmons |
| 2003/0122706 A1 | 7/2003 | Choi et al. |
| 2003/0125616 A1 | 7/2003 | Black et al. |
| 2003/0135127 A1 | 7/2003 | Sackner et al. |
| 2003/0144579 A1 | 7/2003 | Buss |
| 2003/0156288 A1 | 8/2003 | Barnum et al. |
| 2003/0176810 A1 | 9/2003 | Maahs et al. |
| 2003/0189492 A1 | 10/2003 | Harvie |
| 2003/0214408 A1 | 11/2003 | Grajales et al. |
| 2003/0216728 A1 | 11/2003 | Stern et al. |
| 2003/0225323 A1 | 12/2003 | Kiani et al. |
| 2003/0229276 A1 | 12/2003 | Sarussi et al. |
| 2004/0002655 A1 | 1/2004 | Bolorforosh et al. |
| 2004/0004547 A1 | 1/2004 | Appelt et al. |
| 2004/0007585 A1 | 1/2004 | Griffith et al. |
| 2004/0030258 A1 | 2/2004 | Williams et al. |
| 2004/0044545 A1 | 3/2004 | Wiesmann et al. |
| 2004/0054287 A1 | 3/2004 | Stephens |
| 2004/0054291 A1 | 3/2004 | Schulz et al. |
| 2004/0059212 A1* | 3/2004 | Abreu ............ 600/373 |
| 2004/0064097 A1 | 4/2004 | Peterson |
| 2004/0064165 A1 | 4/2004 | Thompson |
| 2004/0082842 A1 | 4/2004 | Lumba et al. |
| 2004/0092919 A1 | 5/2004 | Ritchie et al. |
| 2004/0100784 A1 | 5/2004 | Willers et al. |
| 2004/0102931 A1 | 5/2004 | Ellis et al. |
| 2004/0117891 A1 | 6/2004 | Hannula et al. |
| 2004/0122302 A1 | 6/2004 | Mason et al. |
| 2004/0144391 A1 | 7/2004 | Brady et al. |
| 2004/0147974 A1 | 7/2004 | Engmark et al. |
| 2004/0149282 A1 | 8/2004 | Hickle |
| 2004/0163648 A1 | 8/2004 | Burton |
| 2004/0173456 A1 | 9/2004 | Boos et al. |
| 2004/0186390 A1 | 9/2004 | Ross et al. |
| 2004/0221370 A1 | 11/2004 | Hannula et al. |
| 2004/0230116 A1 | 11/2004 | Cowan et al. |
| 2004/0231772 A1 | 11/2004 | Leonard et al. |
| 2004/0236207 A1 | 11/2004 | Widener et al. |
| 2004/0236242 A1 | 11/2004 | Graham et al. |
| 2004/0242981 A1 | 12/2004 | Pattisapu |
| 2004/0254490 A1 | 12/2004 | Egli |
| 2004/0254501 A1 | 12/2004 | Mault |
| 2004/0260191 A1 | 12/2004 | Stubbs et al. |
| 2004/0263337 A1 | 12/2004 | Terauchi et al. |
| 2004/0267104 A1 | 12/2004 | Hannula et al. |
| 2004/0267145 A1 | 12/2004 | David et al. |
| 2005/0001728 A1 | 1/2005 | Appelt et al. |
| 2005/0020919 A1 | 1/2005 | Stringer et al. |
| 2005/0027207 A1 | 2/2005 | Westbrook et al. |
| 2005/0029432 A1 | 2/2005 | Bacarella et al. |
| 2005/0041531 A1 | 2/2005 | Sekura et al. |
| 2005/0043599 A1 | 2/2005 | O'Mara |
| 2005/0043763 A1 | 2/2005 | Marcovecchio et al. |
| 2005/0049465 A1 | 3/2005 | Wang |
| 2005/0049501 A1 | 3/2005 | Conero et al. |
| 2005/0059869 A1 | 3/2005 | Scharf et al. |
| 2005/0070776 A1 | 3/2005 | Mannheimer et al. |
| 2005/0070778 A1 | 3/2005 | Lakcey et al. |
| 2005/0075550 A1 | 4/2005 | Lindekugel |
| 2005/0080345 A1 | 4/2005 | Finburgh et al. |
| 2005/0085799 A1 | 4/2005 | Luria et al. |
| 2005/0090754 A1 | 4/2005 | Wolff et al. |
| 2005/0096557 A1 | 5/2005 | Vosburgh et al. |
| 2005/0101845 A1 | 5/2005 | Nihtila |
| 2005/0102167 A1 | 5/2005 | Kapoor |
| 2005/0113650 A1 | 5/2005 | Pacione et al. |
| 2005/0113656 A1 | 5/2005 | Chance |
| 2005/0113703 A1 | 5/2005 | Farringdon et al. |
| 2005/0114154 A1 | 5/2005 | Wolkowicz et al. |
| 2005/0171576 A1 | 8/2005 | Williams et al. |
| 2005/0182458 A1 | 8/2005 | Goedeke |
| 2005/0188991 A1 | 9/2005 | Sun et al. |
| 2005/0190068 A1 | 9/2005 | Gentry et al. |
| 2005/0197548 A1 | 9/2005 | Dietiker |
| 2005/0206518 A1 | 9/2005 | Welch et al. |
| 2005/0215847 A1 | 9/2005 | Heruth et al. |
| 2005/0215880 A1 | 9/2005 | Harrison et al. |
| 2005/0215947 A1 | 9/2005 | Heruth et al. |
| 2005/0216064 A1 | 9/2005 | Heruth et al. |
| 2005/0216199 A1 | 9/2005 | Banet |
| 2005/0222522 A1 | 10/2005 | Heruth et al. |
| 2005/0222643 A1 | 10/2005 | Heruth et al. |
| 2005/0228234 A1 | 10/2005 | Yang |
| 2005/0228297 A1 | 10/2005 | Banet et al. |
| 2005/0231686 A1 | 10/2005 | Rathjen |
| 2005/0234312 A1 | 10/2005 | Suzuki et al. |
| 2005/0234317 A1 | 10/2005 | Kiani |
| 2005/0234518 A1 | 10/2005 | Heruth et al. |
| 2005/0240087 A1 | 10/2005 | Keenan et al. |
| 2005/0256523 A1 | 11/2005 | Chen et al. |
| 2005/0261594 A1 | 11/2005 | Banet |
| 2005/0268916 A1 | 12/2005 | Mumford et al. |
| 2005/0277819 A1 | 12/2005 | Kiani et al. |
| 2005/0277821 A1 | 12/2005 | Payne, Jr. |
| 2005/0283082 A1 | 12/2005 | Geddes et al. |
| 2006/0009685 A1 | 1/2006 | Finarov et al. |
| 2006/0009698 A1 | 1/2006 | Banet et al. |
| 2006/0020181 A1 | 1/2006 | Schmidt |
| 2006/0030049 A1 | 2/2006 | Bhimani et al. |
| 2006/0030767 A1 | 2/2006 | Lang et al. |
| 2006/0036179 A1 | 2/2006 | Miller |
| 2006/0047447 A1 | 3/2006 | Brady et al. |
| 2006/0058593 A1 | 3/2006 | Drinan et al. |
| 2006/0058690 A1 | 3/2006 | Bartnik et al. |
| 2006/0064133 A1 | 3/2006 | Von Arx et al. |
| 2006/0064134 A1 | 3/2006 | Mazar et al. |
| 2006/0064142 A1 | 3/2006 | Chavan et al. |
| 2006/0064143 A1 | 3/2006 | Von Arx et al. |
| 2006/0074283 A1 | 4/2006 | Henderson et al. |
| 2006/0074324 A1 | 4/2006 | Wu et al. |
| 2006/0084848 A1 | 4/2006 | Mitchnick |
| 2006/0084852 A1 | 4/2006 | Mason et al. |
| 2006/0085227 A1 | 4/2006 | Rosenfeld et al. |
| 2006/0095032 A1 | 5/2006 | Jackson et al. |
| 2006/0100496 A1 | 5/2006 | Avron |
| 2006/0100530 A1 | 5/2006 | Kliot et al. |
| 2006/0100618 A1 | 5/2006 | Chan et al. |
| 2006/0122517 A1 | 6/2006 | Banet et al. |
| 2006/0122520 A1 | 6/2006 | Banet et al. |
| 2006/0124128 A1 | 6/2006 | Deane et al. |
| 2006/0125623 A1 | 6/2006 | Applet et al. |
| 2006/0132382 A1 | 6/2006 | Jannard |
| 2006/0133362 A1 | 6/2006 | Stein et al. |
| 2006/0142640 A1 | 6/2006 | Takahashi |
| 2006/0149132 A1 | 7/2006 | Iddan |
| 2006/0149339 A1 | 7/2006 | Burnes et al. |
| 2006/0167351 A1 | 7/2006 | Isaacson et al. |
| 2006/0195026 A1 | 8/2006 | Casciani et al. |
| 2006/0195027 A1 | 8/2006 | Casciani et al. |
| 2006/0195028 A1 | 8/2006 | Hannula et al. |
| 2006/0211929 A1 | 9/2006 | Casciani et al. |
| 2006/0217604 A1 | 9/2006 | Fein et al. |
| 2006/0217605 A1 | 9/2006 | Fein et al. |
| 2006/0217606 A1 | 9/2006 | Fein et al. |
| 2006/0217607 A1 | 9/2006 | Fein et al. |
| 2006/0217608 A1 | 9/2006 | Fein et al. |
| 2006/0229510 A1 | 10/2006 | Fein et al. |
| 2006/0229511 A1 | 10/2006 | Fein et al. |
| 2006/0264722 A1 | 11/2006 | Hannula et al. |
| 2006/0264723 A1 | 11/2006 | Hannula et al. |
| 2006/0264724 A1 | 11/2006 | Hannula et al. |
| 2006/0264725 A1 | 11/2006 | Hannula et al. |
| 2006/0264726 A1 | 11/2006 | Mannheimer et al. |
| 2006/0276700 A1 | 12/2006 | O'Neil et al. |
| 2006/0281984 A1 | 12/2006 | Mannheimer et al. |
| 2007/0032732 A1 | 2/2007 | Shelley et al. |
| 2007/0149871 A1 | 6/2007 | Sarussi et al. |
| 2007/0293746 A1 | 12/2007 | Sarussi et al. |
| 2008/0009691 A1 | 1/2008 | Parker |
| 2008/0076988 A1 | 3/2008 | Sarussi et al. |
| 2008/0076990 A1 | 3/2008 | Sarussi et al. |

FOREIGN PATENT DOCUMENTS

| | | |
|---|---|---|
| DE | 3705493 | 8/1988 |
| DE | 3744781 | 1/1989 |
| DE | 3810411 | 10/1989 |
| DE | 3927038 | 2/1991 |
| DE | 4429845 | 10/1995 |
| DE | 29515877 | 11/1995 |
| DE | 19541605 | 5/1997 |
| DE | 19939302 | 5/2001 |
| DE | 10029205 | 1/2002 |
| EP | 0268850 | 6/1988 |
| EP | 0313238 | 4/1989 |
| EP | 338518 | 10/1989 |
| EP | 463620 | 1/1992 |
| EP | 543172 | 5/1993 |
| EP | 0572684 | 12/1993 |
| EP | 0573137 | 12/1993 |
| EP | 578530 | 1/1994 |
| EP | 580385 | 1/1994 |
| EP | 775311 | 8/1994 |
| EP | 0621026 | 10/1994 |
| EP | 0631756 | 1/1995 |
| EP | 0665025 | 8/1995 |
| EP | 0695139 | 2/1996 |
| EP | 0721110 | 7/1996 |
| EP | 1048323 | 2/2000 |
| EP | 996063 | 4/2000 |
| EP | 1130412 | 5/2001 |
| EP | 1169965 | 1/2002 |
| EP | 1683478 | 7/2006 |
| FR | 2555744 | 11/1983 |
| FR | 2601137 | 1/1988 |
| GB | 834469 | 5/1960 |
| GB | 2135074 | 8/1984 |
| GB | 2390903 | 1/2004 |
| JP | 55024614 | 2/1980 |
| JP | 04057161 | 2/1992 |
| JP | 07336597 | 12/1995 |
| JP | 08111295 | 4/1996 |
| JP | 08112257 | 5/1996 |
| JP | 08336546 | 12/1996 |
| JP | 09010319 | 1/1997 |
| JP | 09154937 | 6/1997 |
| JP | 10314149 | 12/1998 |
| JP | 11259583 | 9/1999 |
| JP | 2000189440 | 7/2000 |
| JP | 2001161648 | 6/2001 |
| JP | 2001190498 | 7/2001 |
| JP | 2001308576 | 11/2001 |
| JP | 2001332832 | 11/2001 |
| JP | 2001346775 | 12/2001 |
| JP | 2002065647 | 3/2002 |
| JP | 2003210402 | 7/2003 |
| JP | 2003235813 | 8/2003 |
| JP | 2003265425 | 9/2003 |
| JP | 2004016659 | 1/2004 |
| JP | 2004065832 | 3/2004 |
| JP | 2004121549 | 4/2004 |
| JP | 04258761 | 9/2004 |
| JP | 2005013612 | 1/2005 |
| JP | 2005110816 | 4/2005 |
| JP | 2005111187 | 4/2005 |
| JP | 2005143782 | 6/2005 |
| JP | 2005168600 | 6/2005 |
| JP | 2005266860 | 9/2005 |
| JP | 2006061178 | 3/2006 |
| JP | 2006066512 | 3/2006 |
| JP | 2006122693 | 5/2006 |
| KR | 2002065871 | 8/2002 |
| KR | 2004106928 | 12/2004 |
| RU | 2132204 | 6/1999 |
| WO | WO9001293 | 2/1990 |
| WO | WO9111137 | 8/1991 |
| WO | WO9115151 | 10/1991 |
| WO | WO9118550 | 12/1991 |
| WO | WO9220273 | 11/1992 |
| WO | WO9506430 | 3/1995 |
| WO | WO9512349 | 5/1995 |
| WO | WO9615714 | 5/1996 |
| WO | WO9616591 | 6/1996 |
| WO | WO9641138 | 12/1996 |
| WO | WO9720494 | 6/1997 |
| WO | WO9817174 | 4/1998 |
| WO | WO9947039 | 9/1999 |
| WO | WO9963883 | 12/1999 |
| WO | WO0059374 | 10/2000 |
| WO | WO0078209 | 12/2000 |
| WO | WO0101855 | 1/2001 |
| WO | WO0117425 | 3/2001 |
| WO | WO0176471 | 10/2001 |
| WO | WO0187224 | 11/2001 |
| WO | WO0215784 | 2/2002 |
| WO | WO02065901 | 8/2002 |
| WO | WO02066977 | 8/2002 |
| WO | WO02089664 | 11/2002 |
| WO | WO03026558 | 4/2003 |
| WO | WO03057030 | 7/2003 |
| WO | WO03071928 | 9/2003 |
| WO | WO03080152 | 10/2003 |
| WO | WO2004030480 | 4/2004 |
| WO | WO2004046673 | 6/2004 |
| WO | WO2004084720 | 10/2004 |
| WO | WO2005046466 | 5/2005 |
| WO | WO2005079663 | 9/2005 |
| WO | WO2006007231 | 1/2006 |
| WO | WO2006017117 | 2/2006 |
| WO | WO2006021956 | 3/2006 |
| WO | WO2006094108 | 9/2006 |

* cited by examiner

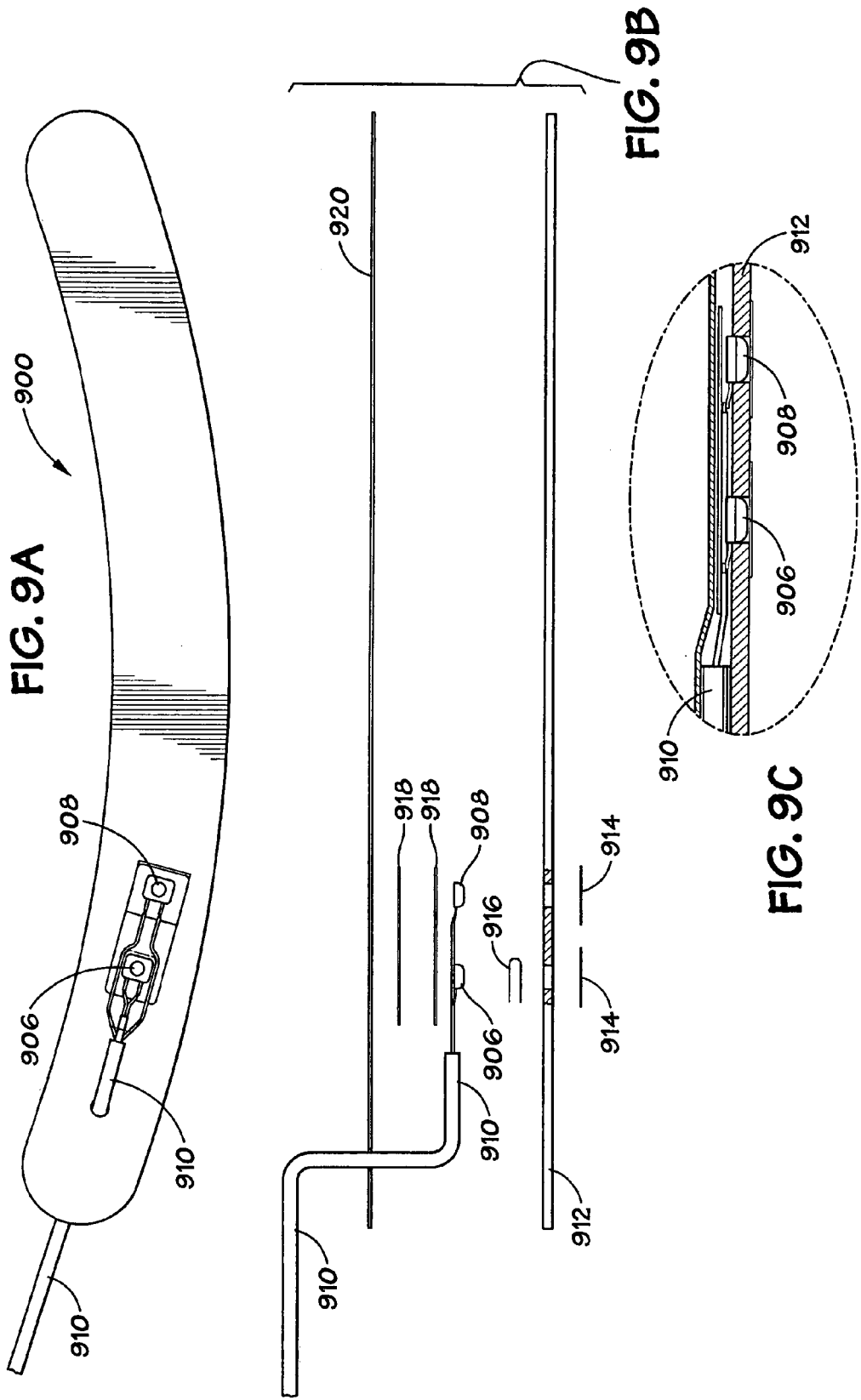

FOREHEAD SENSOR PLACEMENT

CROSS-REFERENCES TO RELATED APPLICATIONS

This application is a continuation of prior U.S. patent application Ser. No. 11/495,195, filed Jul. 28, 2006, which is a division of prior U.S. patent application Ser. No. 10/678,040, filed Oct. 1, 2003, now U.S. Pat. No. 7,289,837, which claims the benefit of U.S. Provisional Patent Application Ser. No. 60/415,468, filed Oct. 1, 2002, which disclosures are incorporated by reference in their entirety for all purposes.

BACKGROUND OF THE INVENTION

The present invention relates to oximetry sensors and in particular to forehead-type oximetry sensors and methods of determining physiological parameters using forehead oximetry sensors.

It is known that the location on a patient's body where an oximetry sensor is applied can have an effect on the estimation of a physiological parameter that is determined using the sensor. It is also known that oximetry measurements can be obtained by placing an oximetry sensor on various locations on the body of a patient, including the fingertips, the earlobe, the foot, the head and so on. In order to have a proper sensor reading, there is a need for ensuring that the sensor is applied to an optimal location on a patient's body; a location where oximetry signals are stable and indicative of the actual physiological parameter which is being monitored.

BRIEF SUMMARY OF THE INVENTION

The present invention is directed towards forehead oximetry sensors and methods of determining physiological parameters using forehead oximetry sensors. In one embodiment, the present invention provides a method of determining a physiological parameter using a pulse oximeter. The method includes placing an oximetry sensor on the forehead of a patient, such that the sensor is placed on the lower forehead region, above the eyebrow with the sensor optics placed lateral of the iris and proximal the temple; and operating the pulse oximeter to obtain the physiological parameter. In one aspect, the method also includes providing and placing a headband over the oximetry sensor. The headband has an elastic segment sized to fit around the patient's head. The headband also includes a non-elastic segment that is smaller than and attached with the elastic segment. The non-elastic segment is sized to span a portion of the elastic segment when the elastic segment is stretched. In addition, the non-elastic segment is larger than the portion of the elastic segment it spans when the elastic segment is not stretched.

In another embodiment, the present invention provides a method for determining a location for the placement of an oximetry sensor. The method includes: measuring the temperature of a plurality of locations on an area of the body of a patient; dividing the temperature measurements into three categories including cold, warm and hot regions, wherein hot areas correspond with areas including those over large movable blood vessels and wherein cold areas correspond with areas including those susceptible to vasoconstriction; and selecting the area that is not hot and not cold as a location for the placement of the sensor.

In another embodiment, the present invention provides a method for determining a location for the placement of an oximetry sensor. The method includes: providing a pulse oximeter having a monitor and a sensor; placing the sensor on a location on the body of a patient; measuring a pulse amplitude using the sensor; comparing the pulse amplitude to a threshold; and recommending a new sensor location using the monitor if the pulse amplitude is lower than the threshold.

In another embodiment, the present invention provides an oximeter sensor, having a substrate having a shape similar to a shape of at least a portion of a patient's forehead and including a section adapted to substantially fit over a portion of a forehead of a patient. The sensor includes an emitter disposed on the substrate at a position located on the section and a detector disposed on the substrate at a distance from the emitter; and a headband for holding the substrate against the patient's forehead, where the headband is sized to fit around the patient's head. In one aspect, the headband includes an elastic segment sized to fit around a patient's head; and a non-elastic segment that is smaller than and attached with the elastic segment. The non-elastic segment is sized to span a portion of the elastic segment when the elastic segment is stretched, and the non-elastic segment is larger than the portion of the elastic segment it spans when the elastic segment is not stretched. In another aspect, the headband's non-elastic segment is sized to not project out from the surface of the elastic portion when the headband is sufficiently tight, thus indicating an adequate level of tension corresponding with delivering a pressure in the range higher than the venous pressure and lower than the capillary pressure to the forehead of the patient.

For a further understanding of the nature and advantages of the invention, reference should be made to the following description taken in conjunction with the accompanying drawings.

BRIEF DESCRIPTION OF THE DRAWINGS

FIG. 9A-F is an assembly drawing of an embodiment of a headband-integrated sensor.

DETAILED DESCRIPTION OF THE INVENTION

Figure 1:
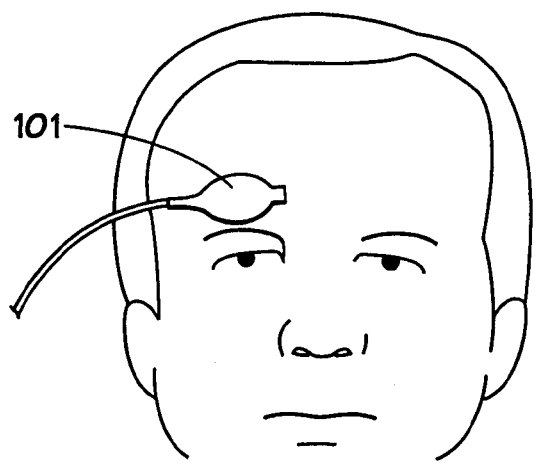
FIG. 1 is a diagram of a forehead oximetry sensor applied to a patient.

The embodiments of the present invention are directed towards forehead oximetry sensors and methods of determining physiological parameters using forehead oximetry sensors. During oximetry, a forehead oximetry sensor 101 (e.g., such as those manufactured by Nellcor Puritan Bennett, the assignee herein), is placed on a patient's forehead, as is shown in FIG. 1. A typical pulse oximeter measures two physiological parameters, percent oxygen saturation of arterial blood hemoglobin (SpO$_2$ or sat) and pulse rate. Oxygen saturation can be estimated using various techniques. In one common technique, the photocurrent generated by the photo-detector is conditioned and processed to determine the ratio of modulation ratios (ratio of ratios) of the red to infrared signals. This modulation ratio has been observed to correlate well to arterial oxygen saturation. The pulse oximeters and sensors are empirically calibrated by measuring the modulation ratio over a range of in vivo measured arterial oxygen saturations (SaO$_2$) on a set of patients, healthy volunteers, or animals. The observed correlation is used in an inverse manner to estimate blood oxygen saturation (SpO$_2$) based on the measured value of modulation ratios of a patient. The estimation of oxygen saturation using modulation ratios is described in U.S. Pat. No. 5,853,364, entitled "METHOD AND APPARATUS FOR ESTIMATING PHYSIOLOGICAL PARAMETERS USING MODEL-BASED ADAPTIVE FILTERING", issued Dec. 29, 1998, and U.S. Pat. No. 4,911,167, entitled "METHOD AND APPARATUS FOR DETECTING OPTICAL PULSES", issued Mar. 27, 1990, and the relationship between oxygen saturation and modulation ratio is further described in U.S. Pat. No. 5,645,059, entitled "MEDICAL SENSOR WITH MODULATED ENCODING SCHEME," issued Jul. 8, 1997, the disclosures of which are herein incorporated by reference in their entirety. Most pulse oximeters extract the plethysmographic signal having first determined saturation or pulse rate.

Figure 2:
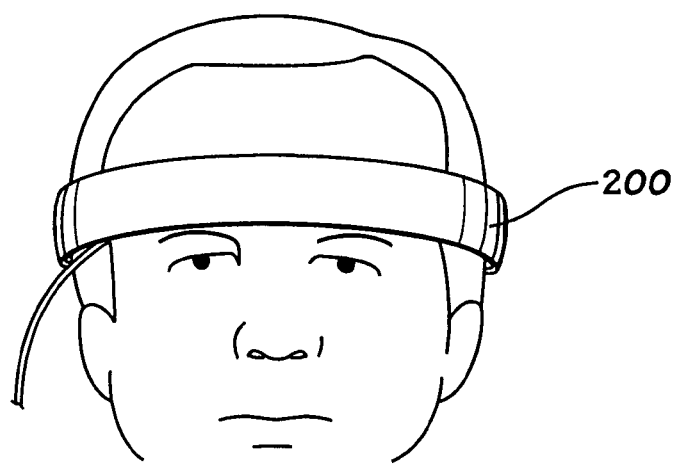
FIG. 2 is a diagram of a forehead oximetry sensor held to a patient's forehead with a headband.

The force applied to the forehead oximetry sensor can be a factor in the proper functioning of the sensor. Generally, a headband is not required to be worn with a forehead oximetry sensor, when the patient's head is upright and/or well above the chest, and/or when the patient has normal venous pressure. In certain clinical scenarios, a headband 200 is required to be used in conjunction with a forehead sensor 101 (e.g., an oximetry sensor), as is shown in FIG. 2. FIG. 2 shows the sensor leads extending from the sensor (not shown) outward from beneath the headband. Such clinical scenarios include scenarios where: patient is lying down with his/her head near or below chest level; patient is subject to elevated venous pressure; patient is diaphoretic; patient is moving excessively, such as during exercise; as well as other scenarios where venous pulsations can introduce errors in oximetry calculations. In those scenarios, without a headband, or force on the oximetry sensor, venous pulsations could cause an incorrect interpretation of the waveform, and therefore result in a less than accurate determination of the oxygen saturation and pulse rate values. The headband can be used to apply pressure to the oximetry sensor, thus reducing the effects of venous pulsations. When used to support an oximetry sensor, the amount of force applied by the sensor on the forehead should be greater than the venous pressure, but less than the arteriole pressure. Generally, a good pressure range is one where the applied pressure is higher than venous pressure (e.g., 3-5 mm Hg) and lower than the capillary pressure (e.g., 22 mm Hg). Preferably, this should be between 15 mm Hg and 20 mm Hg in the adult patient. Exemplary headbands having a pressure or tension indicator are described in a co-pending U.S. patent application Ser. No. 11/495,195, entitled: "FOREHEAD SENSOR PLACEMENT," the disclosure of which is herein incorporated by reference in its entirety for all purposes. As set forth in that co-pending patent application, the headband may be adjusted for use with any size wearer by using an adjustable closure mechanism, such as for example a hook and loop closure mechanism. The user can apply a wide range of pressures to the forehead oximetry sensor depending on the amount of tension which has been applied to the headband during its placement around the wearer's head. In addition, the tension or pressure indicating headband disclosed therein, may be used to help establish an acceptable window of pressure for the sensor's attachment with a patient. The headband when used with a forehead oximetry sensor assists in holding the sensor in place and applies a gentle pressure to expel any pulsating venous blood.

The inventors having conducted various physiological studies have determined that in addition to the possibility of needing to apply an oximetry sensor to the forehead of a patient with a certain amount of pressure, the actual location where the forehead oximetry sensor is applied is also a contributor to the ultimate estimation of physiological parameters determined using the forehead oximeter. An exemplary forehead oximetry sensor is described in a U.S. Pat. No. 6,748,254, entitled: "STACKED ADHESIVE OPTICAL SENSOR," the disclosure of which is herein incorporated by reference in its entirety for all purposes.

The physiological studies conducted by the inventors herein have not only lead to the discovery of preferred locations for the placement of a forehead oximetry sensor, but have also discovered why the forehead and in particular the lower forehead is a preferred sensor location.

Figure 3A:
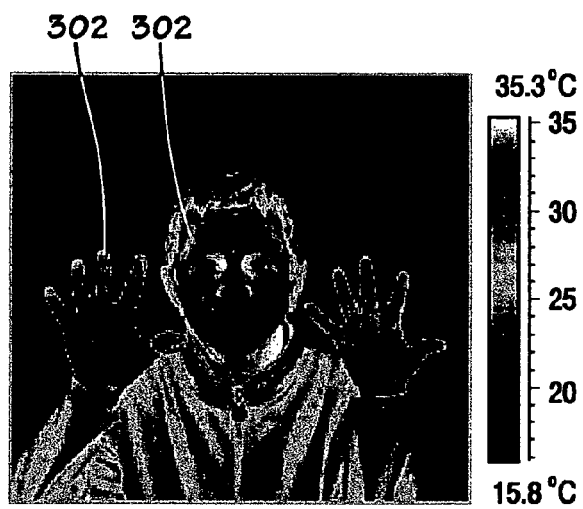
FIGS. 3A-C are thermal images of a person's hands and head in a warm room and after cold room exposure for approximately 45 minutes.
Figure 3B:
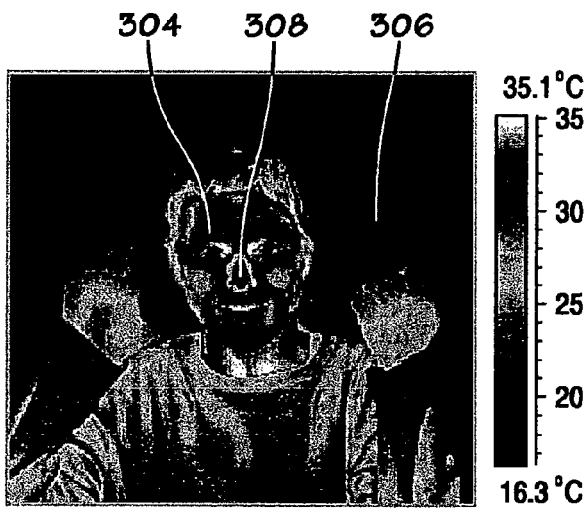
Figure 3C:
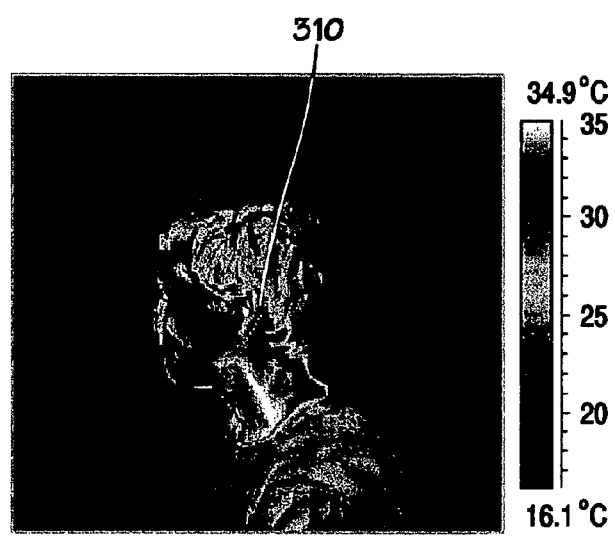

FIGS. 3A-C are thermal images of a person's hands and head in a warm room and after cold room exposure for approximately 45 minutes. These thermal images show warm and cool regions of the head and hands in warm and cold room environments. A cold room environment corresponds with the environment of some operating rooms, whereas a warm room corresponds to other locations. FIG. 3A shows a thermal image of a person's head and hands when the person is located in a room maintained at approximately 72° F. (22° C.) (warm room). As can be seen from this figure, regions 302, which include the head, the fingers and the ears are warm skin regions, indicating regions where there is adequate blood perfusion and hence regions where good oximetry readings can be obtained. In contrast, FIGS. 3B-C show thermal images of the same person as in FIG. 3A, after she has been exposed to a cold room maintained at approximately 58° F. (14.4° C.) for approximately 45 minutes. These figures (FIGS. 3B-C) show that after the exposure to the cold room, region 304, (the head) is the only warm region, whereas the fingers 306, the nose 308 and the ears 310 are cold, indicating regions where there is inadequate blood perfusion and hence regions where poor pulse reading are expected to occur.

Figure 4:
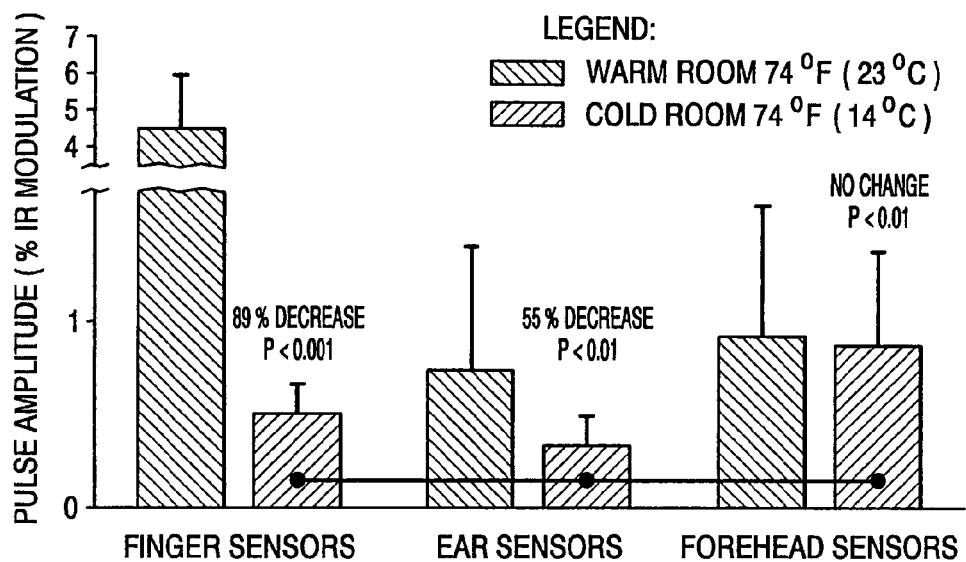
FIG. 4 is a graph showing pulse amplitude signal variations due to a change in the environment's temperature obtained from various sensors located at various locations on a patient's body.

FIG. 4 is a graph showing pulse amplitude signal variations due to a change in the environment's temperature obtained from various sensors located at various locations on a patient's body. This figure shows pulse amplitudes (e.g., % IR [infrared] modulations) obtained using finger, ear, and forehead sensors for humans in a warm room and a cold room. Shown in this figure are the changes in pulse amplitude caused by cold-induced vasoconstriction. As can be seen, the forehead is not significantly affected, while ear and fingers show a strong vasoconstrictive response, because the pulse amplitude obtained by the forehead sensor shows no significant change as the patient is moved from a warm to a cold room. The results of this graph indicate that the lower-forehead region where the forehead sensors were applied provides the most stable pulsatile signal strength of the three sites during vasoconstriction. Other results indicate that the head provides an earlier indication of changes in SaO$_2$ than other sites due to a phenomenon known as circulation delay. This phenomenon provides that hands or fingers, especially in a cold room (e.g., operating room in a surgical unit) see changes in core arterial oxygen saturation events up to a minute later than when it occurs. Clearly such delays can adversely impact a patient's condition.

Figure 5:
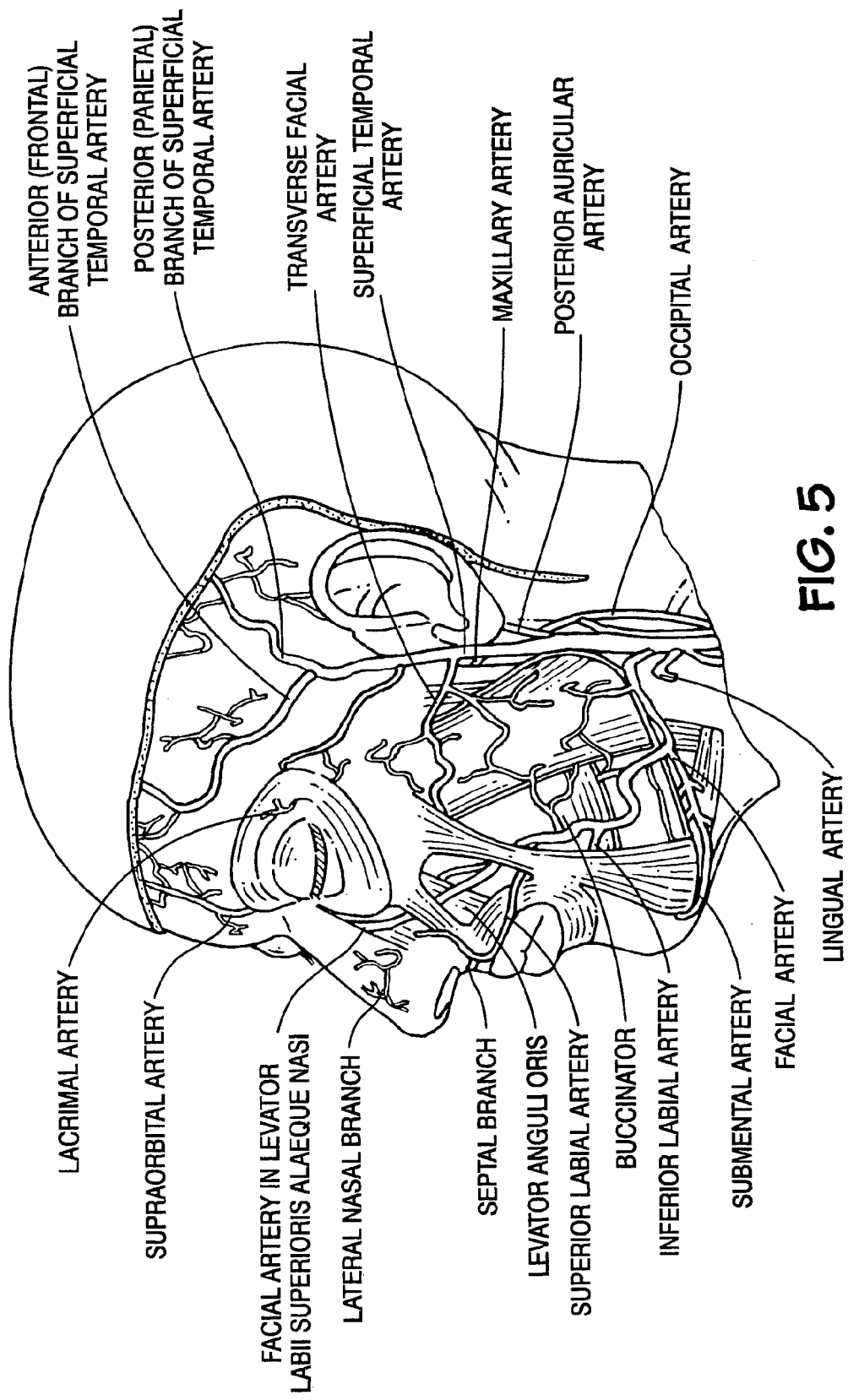
FIG. 5 is a diagram of the arteries in a human head.
Figure 6:
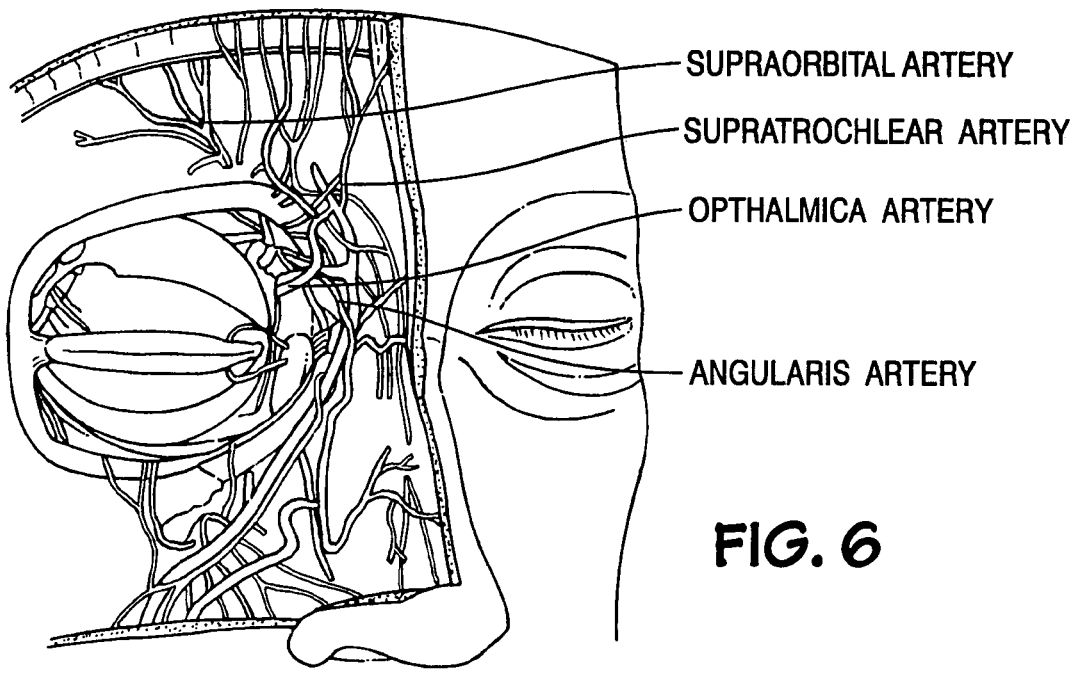
FIG. 6 is a detailed diagram of the arteries around a human eye.

A reason for this vasoconstrictive effect is understood by examining the arteries of the head region, as shown in FIG. 5. This figure shows that the external carotid artery feeds most of the head skin including the ears. The lower-forehead skin is fed by the supraorbital artery, which arises from the internal carotid artery. The external carotid artery does not supply the brain, and the circulation it supports shows more vasoactivity and vasoconstrictor reflexes that the circulation of the lower-forehead region. Referring to FIG. 6, it is shown that the same internal carotid artery source that supplies blood to the eyes and brain supplies the skin directly above the eyebrows. The external carotid artery supplies other facial tissues. Vasoconstrictive response affects the internal branch of the carotid artery less than the external branch of the carotid artery. Therefore, since the lower-forehead blood flow stems from the same circulation that feeds the brain, it is less affected by vasoconstriction, and hence is a more stable and predictable location for oximetry sensor placement.

Figure 7:
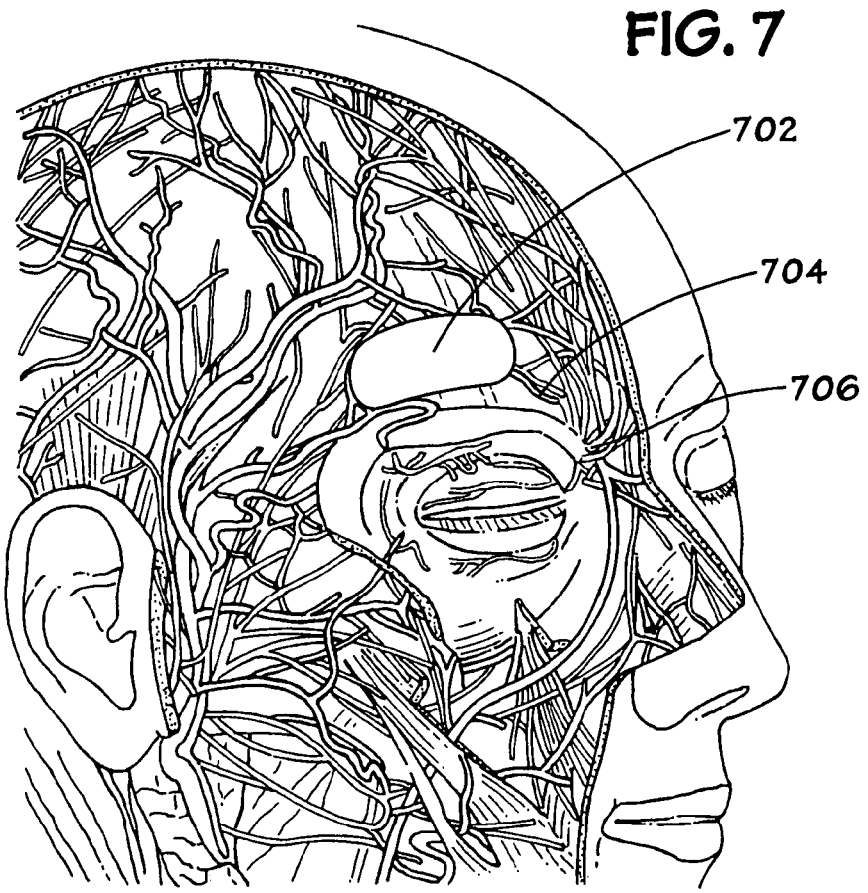
FIG. 7 is a diagram of the arteries in a human head and a preferred location for an oximetry sensor.

Having identified and understood why that the lower forehead region is a preferred location for placing an oximeter sensor, a preferred location on the lower forehead is next described. A preferred sensor placement enables a sensor to optically probe arterial circulation that is fed by the internal carotid artery. In addition, such a preferably-placed sensor probes richly perfused regions of the microvasculature, with little interference from larger blood vessels; and also probes cardiac-induced pulsating arterial blood, with little interference from venous pulsations. FIG. 7 shows such a sensor location to be the lower forehead region 702, immediately above the eyebrow 704, with both the sensor optics (i.e., emitter and detector) located lateral of the iris 706 and proximal the temple. Alternately, the preferred sensor placement is one where the sensor's emitter and the detector are directly above the eyebrow, such that the emitter and detector are both located lateral of the supratrochlear and supraorbital arteries and medial the superficial temporal artery, or in other words, placing the emitter or detector directly above the center of the eye close to the eyebrow, and the other (detector or emitter) approximately horizontally located towards the sides of the head, a few millimeters away (e.g., 2-3 mm to 15 mm). Preferably, the sensor emitter or detector is placed within ±5 mm of the vertical line passing through the location of the iris, more preferably 0 mm-3 mm lateral the iris, and the other of the emitter and detector is placed horizontally lateral this location. Preferably also, the axis connecting the sensor optics is placed within 10 mm of the top of the eyebrow, and more preferably within 5 mm. This placement site is preferred because it experiences little vasoconstriction since the circulation in this region is fed by the internal carotid artery. In addition, this region is preferred because it experiences strong pulsatile signals, with little interference from large blood vessels.

A review of FIG. 7 also shows locations that are less preferred locations for the placement of a forehead sensor. For example, the region of the upper or center of forehead, scalp and facial regions are less preferred region for sensor placement, because this region has superficial vasoactive vessels perfused with blood from external carotid circulation. In addition, sites over large blood vessels, such as the temporal artery are also a lesser-preferred location for sensor placement. For sites over the large blood vessels, the $SpO_2$ readings become unreliable when the sensor light probes large light-absorbing objects that move or change diameter with the heartbeat, where both red and infrared light signals become similarly modulated by the highly opaque vessels, unrelated to the oxygen saturation of arterial blood. Regions over large pulsing blood vessels, such as the temporal and proximal regions of the supraorbital arteries themselves, should preferably not be used as sensor placement sites.

Figure 8:
FIG. 8 is an infrared thermal image of a human head illustrating a proper sensor placement.

FIG. 8 shows an infrared thermal image of a human head illustrating a proper sensor placement. This figure shows the cooler region 802 in and around the nose to be a less preferred location for sensor placement, because the tissue in this region has smaller pulses, and because the region is subject to vasoconstriction. This figure also shows that region 804 being the warmest region is also a lesser preferred region for sensor placement, because the regions directly above larger vessels (hence warmer) are subject to cardio-synchronous vessel movement. In region 804, while the pulsatile signal strength may seem desirable, $SpO_2$ readings could be unreliable. In contrast, region 806, which is above and lateral the center of either eyebrow, is a preferred sensor placement location. As is shown in the figure, a preferred placement for a forehead sensor, such the sensor described in co-pending U.S. patent application Ser. No. 10/256,245, entitled: "Stacked Adhesive Optical Sensor," is to place the emitter above and slightly lateral the iris, with the sensor cable routed back towards the ear. Accordingly, a method for determining a location for the placement of an oximetry sensor, includes: measuring the temperature of a plurality of locations on an area of the body of a patient; dividing the temperature measurements into three categories, namely cold, warm and hot regions; rejecting the hot areas corresponding to areas over large movable blood vessels as a location for the placement of the sensor; rejecting the cold areas corresponding to areas susceptible to vasoconstriction as a location for the placement of the sensor; and selecting the area that is not hot and not cold as a location for the placement of the sensor. The temperature measurement apparatus can be a thermal strip that is made part of the sensor. Alternately, the temperature measurement apparatus may be a part of a sensor attachment device, such as a headband or a hat. Yet alternately, the temperature measurement apparatus may be a separate temperature measurement device packaged with the sensor or the attachment device. Another method for identifying regions over larger cardio-synchronously moving vessels is to palpate the skin; regions in which pulses can be felt to the touch should be avoided, while regions with no or minimal pulsations present represent preferred locations for sensor placement.

In light of the disclosures directed to determining a proper sensor placement location, the sensor's mechanical design itself can be configured for efficient locating on the forehead and above the eye. Such a design has a sensor height (or width) that is smaller than its length. For example, a sensor with a height (or width) smaller than 5 millimeters and length between 6-15 mm satisfies such a configuration. The remaining details of such a sensor are disclosed in the above-referenced and co-pending U.S. patent application Ser. No. 10/256,245, entitled: "Stacked Adhesive Optical Sensor."

As set forth above, an attachment device is described in a co-pending U.S. patent application Ser. No. 11/495,195, entitled: "FOREHEAD SENSOR PLACEMENT." So, in addition to above disclosures directed to the placements of an oximetry sensor, such placements may include the positioning of a headband device over the sensor to hold the sensor in place on the patient's forehead and also to provide a gentle pressure to the forehead sensor.

Figure 9D:
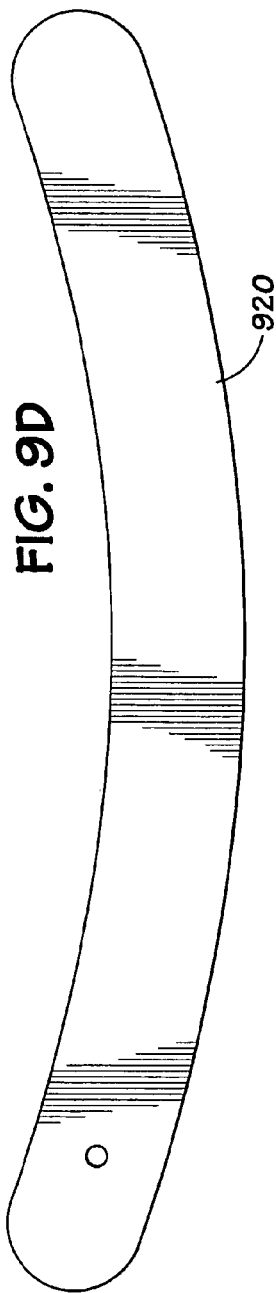
Figure 9E:
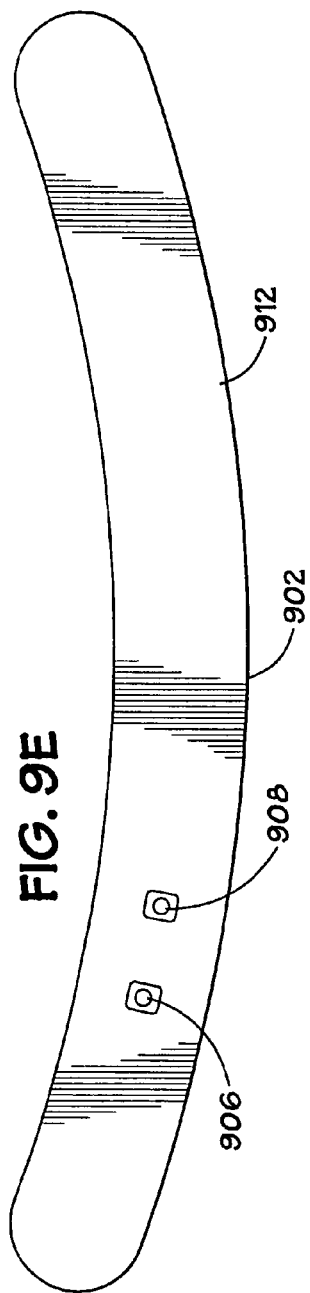
Figure 9F:
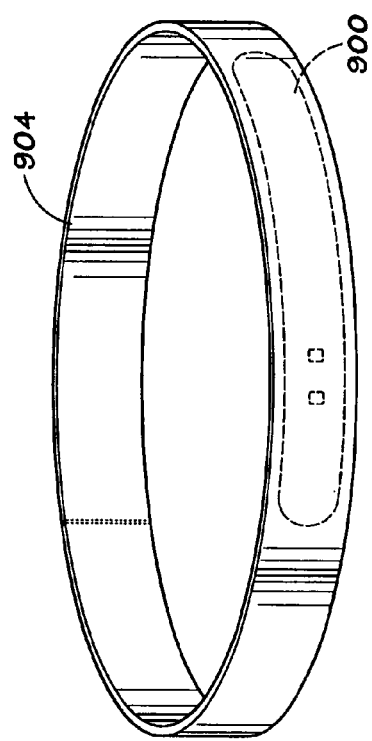

Alternately, the forehead sensor can be integrated with a sensor attachment device, such as a headband. FIG. 9 is an assembly drawing of an embodiment of a headband-integrated sensor. A headband-integrated sensor provides for a more secure and stable placement of a sensor on a patient's forehead than that of two-piece device having a separate sensor and a headband, especially for patient's who move excessively, such as neonate patients. For such patients it is much easier to apply one integrated sensor, as opposed to applying a sensor and then a separate headband over the sensor. FIG. 9 shows an oximeter sensor placed on a substrate 902 that can be placed, adhered, or integrated into a headband 904. In the headband-integrated embodiment, the sensor uses an emitter 906 containing two discrete wavelengths and a detector 908 placed more than 2 mm away, and ideally 10 mm-15 mm from the emitter. The surface 902 can be black in order to minimize any shunting of light between sensor and patient skin. The sensor in a headband could be used in conjunction with a small, portable oximeter to allow mobility of the user during activities. Also shown in FIG. 9 is a cable 910 for providing drive current to the LED and for providing the detector signal to the oximeter. The cable provides the electrical connection to the monitor; it also provides power for the emitter, signal carrying conductors from the detector, and shielding to protect the small signals from the detector against external electrical interference.

The sensor is shown in a multi-layer structure having a face portion 912. The face 912 is the surface that is placed against the patient's skin. The face material may have an adhesive layer such as an acrylic or synthetic rubber adhesive, or it may be without adhesive, and typically made from a foam PVC or foam polyurethane material. The face 912 component is preferably black so as to minimize the incidence of reflected light that does not go through the tissue. Below the face layer 912 are two windows 914. The windows 914 are generally a clear component, such as for example, a thin film or a clear molded plastic component that makes contact with the skin. The thin film window may be a polyurethane or an acrylic adhesive on a polyester film. The intent of the window 914 is to provide an efficient optical coupling mechanism between the optical components (emitter and detector) and the skin. Located above the face 914, is a Faraday shield 916. The Faraday shield 916 is a conductive material, for example, a copper film or copper mesh, that is electrically connected to the monitor ground to help shield the detector from extraneous electrical interference while passing light to the detector. Next located are the LED 906 and the detector 908. Above the LED and the detector is a mask layer, which may include more than one mask layer. The mask layer 918 is generally a thin film that is intended to block light from entering the back side of the sensor, or from traveling directly from emitter to detector (shunt light). The purpose of the mask 918 is to ensure that all of the light reaching the detector is light from the emitter that has traveled through the capillary bed. Above the mask layer 918 is the back layer 920. The back or the top layer is the non-tissue contacting surface of the sensor. This layer may include a cosmetic finish for the sensor, which can be white with some printed artwork identifying the sensor. Typical materials may be Velcro loop, or soft PVC foam.

Figure 10:
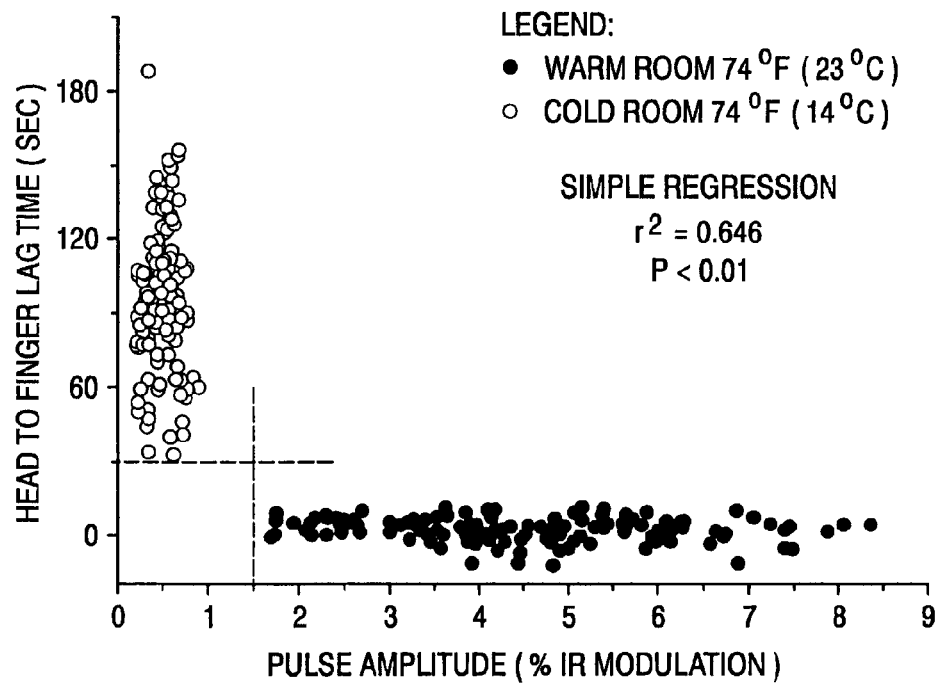
FIG. 10 is a graph of the relationship between Lag Time and Pulse Amplitude.

FIG. 10 is a graph of the relationship between Lag Time in detecting a change in oxygenation status of a patient and Pulse Amplitude. FIG. 10 shows the head to finger time delay in seconds vs. pulse amplitude in % infrared (IR) modulation for values taken in a warm room as well as those taken in a cold room as observed in healthy volunteers. This figure shows a clear clustering of the data points, where the data points taken in a cold room and hence indicative of vasoconstriction all show small pulse amplitude values (e.g., less than 1.5%) and longer head to finger lag times. On the other hand, the data points corresponding to values not impacted by vasoconstriction (warm room data) show a small time lag and larger pulses. Accordingly, a method for determining a location for the placement of an oximetry sensor includes: measuring pulse modulation value, comparing the modulation value to a threshold, and recommending a new sensor location to be chosen by the caregiver. This recommendation has particular value when the initial sensor placement is peripherally located, such as on a finger. The recommendation may be made by the monitor coupled with the sensor using an algorithm being executed by the monitor and communicated to a caregiver using the monitor's audible or visual indicators.

As will be understood by those skilled in the art, the present invention may be embodied in other specific forms without departing from the essential characteristics thereof. These other embodiments are intended to be included within the scope of the present invention, which is set forth in the following claims.

What is claimed is:

1. A method of determining a physiological parameter using a pulse oximeter, comprising:
    placing an oximetry sensor comprising an arcuate substrate having an emitter and a detector on a lower forehead region of a patient, such that the emitter and the detector are placed about a line centered over the iris such that the emitter or the detector is on one side of the iris and that the other of the emitter or the detector is on the other side of the iris; and
    operating the pulse oximeter to obtain the physiological parameter.

2. The method of claim 1, wherein the placing comprises placing the sensor such that an axis connecting the emitter and the detector lies within 8 mm of the top of the patient's eyebrow.

3. The method of claim 1, wherein the placing comprises placing the sensor such that an axis connecting the emitter and the detector lies within 5 mm of the top of the patient's eyebrow.

4. The method of claim 1, wherein the substrate is resilient and has a shape conformable to the lower forehead of the patient.

5. The method of claim 1, wherein the emitter and detector are disposed on the substrate such that an axis connecting the emitter and the detector does not bisect the substrate.

6. The method of claim 1, comprising providing a headband comprising an elastic segment sized to fit around the patient's head and a non-elastic segment being smaller than and attached with the elastic segment, the non-elastic segment sized to span a portion of the elastic segment when the elastic segment is stretched, the non-elastic segment being larger than the portion of the elastic segment it spans when the elastic segment is not stretched; and
    placing the headband over the oximetry sensor.

7. The method of claim 6, wherein the non-elastic segment is attached with the elastic segment in such a manner that the non-elastic segment projects out from the surface of the elastic portion when the headband is not sufficiently tight, thus creating a loop which provides a visual indication that the headband needs re-tightening.

8. The method of claim 1, wherein the physiological parameter is an oxygen saturation value.

9. The method of claim 1, wherein the physiological parameter is a pulse rate.

10. A system comprising:
    a monitor configured to determine a physiological parameter based at least in part upon a signal related to the physiological parameter; and
    a sensor coupled to the monitor and capable of generating the signal related to the physiological parameter, the sensor comprising:
        a substrate being adapted to directly contact a portion of a forehead of a patient, wherein the substrate is arcuate when placed flat upon a planar surface in the absence of any restraining force;
an emitter and a detector disposed on the substrate; and
a headband configured to hold the substrate against the patient's forehead, the headband sized to fit around the patient's head, wherein the headband comprises:
an elastic segment sized to fit around a patient's head; and
a non-elastic segment being smaller than and attached with the elastic segment, wherein the exterior side of the elastic segment generally faces away from the wearer when the headband is applied to the wearer's head, and the non-elastic segment sized to span a portion of the elastic segment when the elastic segment is stretched, the non-elastic segment being larger than the portion of the elastic segment it spans when the elastic segment is not stretched, wherein the non-elastic segment is sized to not project out from the surface of the elastic portion when the headband is sufficiently tight thus indicating an adequate level of tension corresponding with delivering a pressure in the range higher than the venous pressure and lower than the capillary pressure to the forehead of the patient.

11. The system of claim 10, wherein the substrate is resilient and has a shape conformable to the forehead of a patient.

12. The system of claim 10, wherein the substrate is adhered to the inside of the headband.

13. The system of claim 10, wherein the physiological parameter is an oxygen saturation value.

14. The system of claim 10, wherein the physiological parameter is a pulse rate.

15. The system of claim 10, wherein the headband comprises a closure mechanism coupled with the elastic portion.

16. The system of claim 15, wherein the closure mechanism is a hook and loop closure, a snap, a button, an adhesive, a pin, or any combination thereof.

17. The system of claim 10, wherein the elastic segment is rectangular shaped having a long and a short dimension, and the non-elastic segment is attached along a set of its edges with the elastic segment, wherein the set of edges are generally parallel to the short dimension.

18. The system of claim 10, wherein the non-elastic segment is attached with the elastic segment in such a manner that the non-elastic segment projects out from
the surface of the elastic portion when the headband is not sufficiently tight, thus creating a loop which provides a visual indication that the headband needs re-tightening.

* * * * *